US006165483A

United States Patent [19]

Hei et al.

[11] Patent Number: 6,165,483

[45] Date of Patent: Dec. 26, 2000

[54] PEROXY ACID TREATMENT TO CONTROL PATHOGENIC ORGANISMS ON GROWING PLANTS

[75] Inventors: Robert D. P. Hei, Oakdale; Leanne J. Adkins, Eagan; Keith D. Lokkesmoe, Savage; Heidi M. Hanson, Minneapolis; Bruce R. Cords, Eagan, all of Minn.

[73] Assignee: Ecolab Inc., St. Paul, Minn.

[21] Appl. No.: 09/055,609

[22] Filed: Apr. 6, 1998

[51] Int. Cl.$^7$ .................................................... A01N 25/02

[52] U.S. Cl. ............................ 424/405; 424/616; 424/44; 504/100; 504/101; 504/113; 504/114; 504/125; 504/320; 514/155; 514/517; 514/518; 514/557; 514/558; 514/560

[58] Field of Search .................................... 514/558, 560, 514/559, 557, 155, 576, 577, 510, 517, 518, 578; 424/44, 600, 616, 405, 406; 504/100–102, 113, 114, 125, 320

[56] References Cited

U.S. PATENT DOCUMENTS

| | | | |
|---|---|---|---|
| 1,589,866 | 6/1926 | Siegler et al. | 514/558 |
| 1,955,052 | 4/1934 | Burwell | 514/558 |
| 2,512,640 | 6/1950 | Greenspan et al. . | |
| 3,333,942 | 8/1967 | Hartley et al. | 514/558 |
| 4,051,059 | 9/1977 | Bowing et al. . | |
| 5,168,655 | 12/1992 | Davidson et al. . | |
| 5,200,189 | 4/1993 | Oakes et al. . | |
| 5,314,687 | 5/1994 | Oakes et al. . | |
| 5,437,868 | 8/1995 | Oakes et al. . | |
| 5,489,434 | 2/1996 | Oakes et al. . | |
| 5,674,538 | 10/1997 | Lokkesmoe et al. | 424/616 |

FOREIGN PATENT DOCUMENTS

| | | |
|---|---|---|
| 9300538 | 11/1994 | Denmark . |
| 0 233 731 A2 | 8/1987 | European Pat. Off. . |
| 0 242 990 A2 | 10/1987 | European Pat. Off. . |
| 0 361 955 A2 | 4/1990 | European Pat. Off. . |
| 3003875 | 8/1981 | Germany . |
| 70-31210 | 2/1995 | Japan . |
| 72-58005 | 10/1995 | Japan . |
| 2187958 | 9/1987 | United Kingdom . |
| 2257630 | 1/1993 | United Kingdom . |
| WO 93/01716 | 2/1993 | WIPO . |
| WO 94/06294 | 3/1994 | WIPO . |
| WO 94/21122 | 9/1994 | WIPO . |
| WO 94/23575 | 10/1994 | WIPO . |

*Primary Examiner*—Neil S. Levy
*Attorney, Agent, or Firm*—Merchant & Gould P.C.

[57] ABSTRACT

Both a process and a method of using peracid compositions, especially mixed peracid systems, to treat field or greenhouse grown plant tissue, seeds, fruits, and growing media and containers. The peracid can lower the natural, plant pathogen and human pathogenic microbial load resulting in less waste to molding, spoilage, and destruction because of pathogenic poisons.

24 Claims, No Drawings

PEROXY ACID TREATMENT TO CONTROL PATHOGENIC ORGANISMS ON GROWING PLANTS

FIELD OF THE INVENTION

The invention relates to a process of using peracid compositions, especially mixed peracid systems, to treat field, hydroponic or greenhouse growing plant tissue, seeds, fruits, growing media and containers. The peracid can lower the natural, plant pathogen and human pathogenic microbial load resulting in less waste to molding, spoilage, and destruction because of pathogenic poisons.

BACKGROUND OF THE INVENTION

In the production of fruits and vegetables, plants can be grown in the field, in greenhouses, and hydroponically. Each location has its own growing medium, environment and growing conditions. Agricultural personnel work to maximize production by maximizing growing conditions while minimizing attack on seeds, seedlings, plants and fruit by living pests. Such pests include insects, rodents, bacteria, fungi, etc.

Substantial attention has been given to antimicrobial compounds that attack bacteria and fungi on seeds, seedlings, growing plants and fruit in the production cycle on growing plants. The use of fungicides in agriculture is necessitated by the great losses caused by a wide variety of plant-pathogenic microorganisms. To be economic, the costs of controlling plant diseases by the application of bactericides and fungicides must be offset by potential gains of several fold. Large tonages of fungicides are required in the agriculture of apples, pears, bananas, cereals, cocoa, coffee, cotton, potatoes, tobacco, grapes, sprouts and other common fruits and vegetables including celery, leeks, onions, lettuce, spinach, brussel sprouts, potatoes, truffles, garlic, shallots, peppers, beans, tomatoes, almonds, pears, apples, peanuts and others. Fungicides are typically applied in water suspension with hydraulic sprayers or in the form of dust, granules or fumigants. Early fungicides included sulfur and polysulfides, heavy metals and others. Such harsh fungicides have been replaced by newer but still toxic materials such as quinones, organosulfur compounds, imidazolines and guanidines, trichloromethylthiocarboximides, chlorinated and nitrated benzenes, oxithines, benzimidazoles, pyrimidines, and others. These broad spectrum protectant materials effect enzyme and membrane systems of the target microorganism. Typically, the mode of action includes inhibition of fungal or bacterial energy production, interference with biosynthesis or disruption of cell membrane structure.

The above fungicides have had some success; however, they are viewed as toxic materials and a substantial quantity of plant produce is wasted due to their deliterious effect. Accordingly, a substantial need exists to continue to develop antimicrobial materials that can protect growing plants including seeds, cuttings, seedlings, growing plants, plant parts, fruit, and other agricultural produce.

Peroxy Acids

Further, human and plant pathogenic bacteria and fungi can be a contamination problem in growing plants. We have found *coli* form, salmonella, and other bacteria common in the agricultural and greenhouse environment can contaminate growing plants and pose a threat to human health in consumption of fresh vegetables, fruit and produce. A substantial need exists for treatments that can reduce bacterial contamination.

Peroxy acids are strong oxidizers and have the simple general structure given as formula (1), where R can be essentially any hydrocarbon group:

(1)

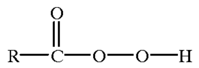

Antimicrobial Treatments

Peroxy-containing compositions are known for use in the production of microbicidal agents. One such composition is disclosed in Bowing et al., U.S. Pat. No. 4,051,059 containing peracetic acid, acetic acid or mixtures of peracetic and acetic acid, hydrogen peroxide, anionic surface active compounds such as sulfonates and sulfates, and water.

Peracetic acid has been shown to be a good biocide, but only at fairly high concentrations (generally greater than 100 parts per million (ppm)). Similarly, peroxyfatty acids have also been shown to be biocidal, but only at high concentrations (greater than 200 ppm), such as in the composition disclosed in European Patent Application No. 233,731.

GB 2187958 A and EU 0242990 A2 describe the use of either peracetic or perpropionic acid for controlling plant pathogens on flowers and fruit tissue. They are directed to edible field-grown plants and cereal crops.

WO 94/06294 describes the use of a single peracid composition along with mixtures of aliphatic acids for vegetable disinfection.

U.S. Pat. No. 5,168,655 relates to hydroponic treatment using peracids. The reference describes peracid treatments of hydroponic growing substrates (e.g., rock wool) prior to growth; i.e., the growth substrate is treated after a crop production cycle and prior to a subsequent crop-production cycle. In contrast, the present invention describes hydroponic treatment during the growth cycle.

U.S. Pat. No. 5,200,189 to Oakes et al. describes use of mixed peracid compositions to enhance microbial kill for hard surface sanitizing. Certain mixed peracids have now been found useful to enhance microbial kill on sensitive growing plant tissue or its harvested fruiting matter.

U.S. Pat. No. 2,512,640 to Greenspan et al. discloses the use of single peracid compositions to enhance microbial reduction on produce, reduce produce browning, and prevent spoilage. Greenspan does not disclose any mixed peracid synergies and applies the peracid only to harvested fruit.

GB 2257630A describes the use of a single peracid which is activated by an activator (Fe, Cu, Br, I) for controlling microbial counts on hard surfaces, effluent waters and growing plant tissues. Again, this is a single peracid composition which fails to teach synergies between mixed peracids.

DK 9300538 describes the use of peracetic acid, followed by a biological combat, for controlling pathogens in recirculating watering systems to plant crops. This reference does not describe any direct crop treatments.

JP 07031210 teaches the use of 5 to 200 ppm peracetic and or perpropionic acids for treatment of seedling culture medium prior to planting; specifically for the control of slime, algae or fungi on the culture medium. The teaching is limited to the use of $C_2$ and $C_3$ acids and has no application to growing plant tissue.

JP 07258005 A teaches the use of high levels (1000 ppm) of peracetic acid for controlling bacteria on rice. This application is intended only to effect disease control and not for hydroponic growth of the grain matter.

DE 3003875 A describes the use of $C_1$–$C_4$ peracids and hydrogen peroxide to control phytopathogenic pests on soil. This reference does not disclose any direct application to plants.

BRIEF DESCRIPTION OF THE INVENTION

We have found that a mixed peracid treatment composition can be used to protect growing plant tissue from the undesirable effects of microbial attack. The mixed peracid materials used in this invention can be applied to growing plant tissues and can provide residual antimicrobial effects after the plant has completed its growth cycle, fruit or vegetable material have been harvested and sent to market. The materials of the invention have been found to be excellent antimicrobial compounds but pose little toxic effects to agricultural workers or the ultimate consumer.

We have found that peroxy acid materials can be an effective treatment of living or growing plant tissues including seeds, roots, tubers, seedlings, cuttings, rooting stock, growing plants, produce, fruits and vegetables, etc. Under certain circumstances, a single peroxyacid material can be effective, however, in other circumstances, a mixed peroxy acid has substantially improved and surprising properties.

The invention involves a peroxyacid antimicrobial concentrate and diluted end use composition including an effective microbicidal amount of a $C_2$–$C_4$ peroxycarboxylic acid such as peracetic acid, an effective microbicidal amount of a $C_5$–$C_{12}$ peroxyacid, preferably with a $C_6$–$C_{12}$ or a $C_8$–$C_{12}$ peroxy acid, or mixtures thereof. The concentrate composition can be diluted with a major proportion of water to form an antimicrobial sanitizing use solution having a pH in the range of about 2 to 8, with a $C_2$–$C_4$ peroxycarboxylic acid concentration of at least about 4 ppm, preferably about 10 to 75 ppm, and a $C_5$–$C_{12}$, a $C_6$–$C_{12}$, or a $C_8$–$C_{12}$ peroxyacid concentration of at least about 1 ppm, preferably about 1 to 25 ppm. Other components may be added such as a hydrotrope coupling agent for solubilizing the peroxyfatty acid in the concentrate form and when the concentrate composition is diluted with water.

The invention involves a method of controlling fungi and microbial plant pathogens in growing plants by treating said growing plants with a dilute aqueous solution comprising an effective amount of a $C_2$–$C_4$ peroxycarboxylic acid and an aliphatic $C_5$–$C_{12}$, a $C_6$–$C_{12}$ or a $C_8$–$C_{12}$ peroxycarboxylic acid.

The invention further involves a process for controlling fungi and microbial plant pathogens in growing plants by diluting in an aqueous liquid a concentrate containing: about 1 to 20 wt-% of a $C_2$–$C_4$ peroxycarboxylic acid; about 0.1 to 20 wt-% of an aliphatic $C_5$–$C_{12,}$ a $C_6$–$C_{12}$ or a $C_8$–$C_{12}$ peroxycarboxylic acid to form a solution; and contacting said growing plants with said solution.

The invention further involves a process for controlling fungi and microbial plant pathogens in growing plants by diluting in an aqueous liquid a concentrate containing: about 1 to 20 wt-% of a $C_2$–$C_4$ peroxycarboxylic acid; about 0.1 to 20 wt-% of an aliphatic $C_5$–$C_{12}$, a $C_6$–$C_{12}$ or a $C_8$–$C_{12}$ peroxycarboxylic acid; about 5 to 40 wt-% of a $C_2$–$C_4$ carboxylic acid; about 1 to 20 wt-% of an aliphatic $C_8$–$C_{12}$ carboxylic acid; and about 1 to 30 wt-% of hydrogen peroxide to form a solution; and contacting said growing plants with said solution.

In contrast to the prior art, we have discovered that at a low pH, (e.g. preferably less than 7) $C_{5+}$ peroxyacids such as peroxyfatty acids are very potent biocides at low levels when used in combination with a $C_2$–$C_4$ peroxycarboxylic acid such as peroxyacetic acid, a synergistic effect is obtained, providing a much more potent biocide than can be obtained by using these components separately. This means that substantially lower concentrations of biocide can be used to obtain equal biocidal effects.

As the term is used herein, a $C_5$–$C_{12}$ peroxyacid (or peracid) is intended to mean the product of the oxidation of a $C_5$–$C_{12}$ acid such as a fatty acid, or a mixture of acids, to form a peroxyacid having from about 5 to 12 carbon atoms per molecule. The $C_5$–$C_{12}$ peroxyacids are preferably aliphatic (straight or branched).

Peroxycarboxylic acid is intended to mean the product of oxidation of a $C_2$–$C_4$ carboxylic acid, or a mixture thereof. This includes both straight and branched $C_2$–$C_4$ carboxylic acids.

The claimed invention includes a method of controlling fungi and microbial plant pathogens in growing plants. This treatment utilizes a combination of two different peroxy acids. This mixture comprises at least 4 parts per million (ppm) of a smaller $C_2$–$C_4$ peroxy carboxylic acid and at least 1 ppm of a larger $C_5$–$C_{12}$ peroxy carboxylic acid. The preferred mixture comprises at least 4 ppm of a smaller $C_2$–$C_4$ peroxy acid and at least 1 ppm of a large aliphatic $C_8$–$C_{12}$ peroxy acid.

An especially preferred embodiment of the composition includes a mixture of peroxyacetic acid (given as formula (2)) and peroctanoic acid (given here as formula (3)).

(2)

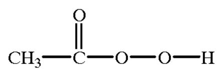

(3)

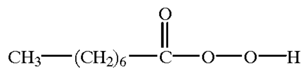

The composition also may contain a hydrotrope for the purpose of increasing the aqueous solubility of various slightly soluble organic compounds. The preferred embodiment of the invention utilizes a hydrotrope chosen from the group of n-octanesulfonate, a xylene sulfonate, a naphthalene sulfonate, ethylhexyl sulfate, lauryl sulfate, an amine oxide, or a mixture thereof.

The composition may also contain a chelating agent for the purpose of removing ions from solution. The preferred embodiment of the invention uses 1-hydroxyethylidene-1, 1-diphosphonic acid.

Further, the invention also provides a process of controlling fungi and microbial plant pathogens in growing plants. In this embodiment, the plant is contacted with a solution made by diluting in an aqueous liquid a concentrate comprising two peroxy acids. This mixture includes $C_2$–$C_4$ peroxy carboxylic acid and a larger $C_8$–$C_{12}$ peroxy carboxylic acid. The preferred mixture includes about 1–20 weight percent (wt %) of a smaller $C_2$–$C_4$ peroxy acid and about 0.1–20 wt % of a larger $C_8$–$C_{12}$ peroxy acid. An especially preferred embodiment of the composition includes a mixture of peroxyacetic acid and peroxyoctanoic acid. The composition may further contain about 1–15 wt % of a hydrotrope and about 5 wt-% of a chelating agent.

Finally, the invention also provides a process of controlling fungi and microbial plant pathogens in growing plants. In this embodiment, the plant is contacted with a solution made by diluting in an aqueous liquid a concentrate containing two peroxy acids. This mixture includes a smaller $C_2$–$C_4$ peroxy carboxylic acid and a larger $C_8$–$C_{12}$ aliphatic peroxy carboxylic acid. An especially preferred embodiment of the composition includes a mixture of peroxyacetic acid and peroctanoic acid. The composition may further contain a hydrotrope and a chelating agent. Further, the solution contains about 1–30 wt % of hydrogen peroxide ($H_2O_2$). The preferred composition includes a mixture of acetic acid (formula (4)) and octanoic acid (formula (5)).

(4)

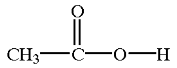

(5)

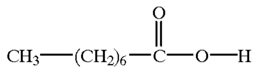

DETAILED DESCRIPTION OF THE INVENTION

Peracids

We have found surprisingly that peroxy acid compounds of the invention can be contacted directly with living plant tissue in the form of a seed, a cutting, a root stock, graft, tuber juvenile or adult plant and reduced microbial populations without substantially affecting the health of the living tissue.

The invention is also based upon the surprising discovery that when a $C_5$–$C_{12}$ peroxyacid is combined with a $C_2$–$C_4$ peroxycarboxylic acid, a synergistic effect is produced and greatly enhanced antimicrobial activity is exhibited when compared to the $C_8$–$C_{12}$ peroxyacid or the $C_2$–$C_4$ peroxycarboxylic acid alone. The present blend of a $C_8$–$C_{12}$ peroxyacid and a $C_2$–$C_4$ peroxycarboxylic acid can effectively kill microorganisms (e.g., a 5 $\log_{10}$ reduction in 30 seconds) from a concentration level below 100 ppm and as low as 20 ppm of the peracid blend.

A variety of $C_5$–$C_{12}$ peroxyacids may be employed in the composition of the invention such as peroxyfatty acids, monoperoxy- or diperoxydicarboxylic acids, and peroxyaromatic acids. The $C_5$–$C_{12}$ peroxyacids employed in the present invention may be structurally represented as: $R_1$—$CO_3H$, wherein $R_1$ is a hydrocarbon moiety having from about 4 to 11 carbon atoms. $R_1$ may have substituents in the chain, e.g., —OH, $CO_2H$, or heteroatoms (e.g., -0-as in alkylether carboxylic acids), as long as the antimicrobial properties of the overall composition are not significantly affected. It should be recognized that "$R_1$" substituents or heteroatoms may change the overall acidity (i.e., pKa) of the carboxylic acids herein described. Such modification is within the contemplation of the present invention provided the advantageous antimicrobial performance is maintained. Furthermore, $R_1$ may be linear, branched, cyclic or aromatic. Preferred hydrocarbon moieties (i.e. preferred $R_1$'s) include linear, saturated, hydrocarbon aliphatic moieties having from 7 to 11 carbon atoms (or 8 to 12 carbon atoms per molecule).

Specific examples of suitable $C_8$–$C_{12}$ carboxylic fatty acids which can be reacted with hydrogen peroxide to form peroxyfatty acids include such saturated fatty acids as caprylic (octanoic) ($C_8$), pelargonic (nonanoic) ($C_9$), capric (decanoic) ($C_{10}$), undecyclic (undecanoic) ($C_{11}$), lauric (dodecanoic) ($C_{12.}$ These acids can be derived from both natural and synthetic sources. Natural sources include animal and vegetable fats or oils which should be fully hydrogenated. Synthetic acids can be produced by the oxidation of petroleum wax. Particularly preferred peroxyfatty acids for use in the composition of the invention are linear monoperoxy aliphatic fatty acids such as peroxyoctanoic acid, peroxydecanoic acid, or mixtures thereof.

Other suitable peroxyacids are derived from the oxidation of dicarboxylic acids and aromatic acids. Suitable dicarboxylic acids include sebacic acid ($C_{10}$). An example of a suitable aromatic acid is benzoic acid. These acids can be reacted with hydrogen peroxide to form the peracid form suitable for use in the composition of the invention. Preferred peracids in this group include monoperoxy- or diperoxyadipic acid, monoperoxy- or diperoxysebacic acid, and peroxybenzoic acid.

The above peroxyacids provide antibacterial activity against a wide variety of microorganisms, such as gram positive (e.g., *Staphylococcus aureus*) and gram negative (e.g., *Escherichia coli*, salmonella, etc.) microorganisms, yeast, molds, bacterial spores, etc. When the above $C_5$–$C_{12}$ peroxyacids are combined with a $C_2$–$C_4$ peroxycarboxylic acid, greatly enhanced activity is shown compared to the $C_2$–$C_4$ peroxycarboxylic acid alone or the $C_8$–$C_{12}$ peroxyacid alone. The $C_2$–$C_4$ peroxycarboxylic acid component can be derived from a $C_2$–$C_4$ carboxylic acid or dicarboxylic acid by reacting the acid, or the corresponding anhydride or acid chloride, with hydrogen peroxide. Examples of suitable $C_2$–$C_4$ carboxylic acids include acetic acid, propionic acid, glycolic acid, and succinic acid or their corresponding anhydrides or acid chlorides. Preferable $C_2$–$C_4$ peroxycarboxylic acids for use in the composition of the invention include peroxyacetic acid, peroxypropionic acid, peroxyglycolic acid, peroxysuccinic acid, or mixtures thereof.

The antimicrobial concentrate of the present invention can comprise about 0.1 to 20 wt. %, preferably about 0.1 to 5 wt. %, and most preferably about 0.1 to 2 wt. % of a $C_8$–$C_{12}$ peroxyacid, and about 1 to 20 wt. %, preferably about 1 to 15 wt. % and most preferably 4–15 wt. % of a $C_2$–$C_4$ peroxycarboxylic acid. The concentrate composition preferably has a weight ratio of $C_2$–$C_4$ peroxycarboxylic acid to $C_8$–$C_{12}$ peroxyacid of about 15:1 to 1:1. The concentrate contains sufficient acid so that the end use solution has a pH of about 2 to 8, preferably about 3 to 7. Some acidity may come from an inert acidulant which may be optionally added (e.g., sulfuric or phosphoric acid).

The peracid components used in the composition of the invention can be produced in a simple manner by mixing a hydrogen peroxide ($H_2O_2$) solution, or by utilizing powdered peroxide generators such as percarbonates or perborates, with the desired amount of acid. With the higher molecular weight fatty acids, a hydrotrope coupler may be required to help solubilize the fatty acid. The $H_2O_2$ solution also can be added to previously made peracids such as peracetic acid or various perfatty acids to produce the peracid composition of the invention. The concentrate can contain about 1 to 30 wt. %, preferably about 5 to 25 wt. % of hydrogen peroxide.

The concentrate composition can further comprise a free $C_8$–$C_{12}$ carboxylic acid, a free $C_2$–$C_4$ carboxylic acid, or mixtures thereof. The free acids will preferably correspond to the starting materials used in the preparation of the peroxyacid components. The free $C_8$–$C_{12}$ carboxylic acid is preferably linear and saturated, has 8 to 12 carbon atoms per molecule, and can also comprise a mixture of acids. The free $C_8$–$C_{12}$ carboxylic acid and free $C_2$–$C_4$ carboxylic acid can be present as a result of an equilibrium reaction with the hydrogen peroxide to form the peroxyacids.

Other Components

Various optional materials may be added to the composition of the invention to help solubilize the fatty acids, restrict or enhance the formation of foam, to control hard water, to stabilize the composition, or to further enhance the antimicrobial activity of the composition.

The composition of the invention can contain a surfactant hydrotrope coupling agent or solubilizer that permits blending short chain perfatty acids in aqueous liquids. Functionally speaking, the suitable couplers which can be employed are non-toxic and retain the fatty acid and the perfatty acid in aqueous solution throughout the temperature range and concentration to which a concentrate or any use solution is exposed.

Any hydrotrope coupler may be used provided it does not react with the other components of the composition or negatively affect the antimicrobial properties of the composition. Representative classes of hydrotropic coupling agents or solubilizers which can be employed include anionic surfactants such as alkyl sulfates and alkane sulfonates, linear alkyl benzene or naphthalene sulfonates, secondary alkane sulfonates, alkyl ether sulfates or sulfonates, alkyl phosphates or phosphonates, dialkyl sulfosuccinic acid esters, sugar esters (e.g., sorbitan esters), amine oxides (mono-, di-, or tri-alkyl) and $C_8$–$C_{10}$ alkyl glucosides. Preferred coupling agents for use in the present invention include n-octanesulfonate, available as NAS 8D from Ecolab, n-octyl dimethylamine oxide, and the commonly available aromatic sulfonates such as the alkyl benzene sulfonates (e.g. xylene sulfonates) or naphthalene sulfonates.

Some of the above hydrotropic coupling agents independently exhibit antimicrobial activity at low pH. This adds to the efficacy of the present invention, but is not the primary criterion used in selecting an appropriate coupling agent. Since it is the presence of perfatty acid in the protonated neutral state which provides biocidal activity, the coupling agent should be selected not for its independent antimicrobial activity but for its ability to provide effective interaction between the substantially insoluble perfatty acids described herein and the microorganisms which the present compositions control.

The hydrotrope coupling agent can comprise about 0.1 to 30 wt. %, preferably about 1 to 15 wt. %, and most preferably about 2 to 15 wt. % of the concentrate composition.

Compounds such as mono, di and trialkyl phosphate esters may be added to the composition to suppress foam. Such phosphate esters would generally be produced from aliphatic linear alcohols, there being from 8 to 12 carbon atoms in the aliphatic portions of the alkyl phosphate esters. Alkyl phosphate esters possess some antimicrobial activity in their own right under the conditions of the present invention. This antimicrobial activity also tends to add to the overall antimicrobial activity of the present compositions even though the phosphate esters may be added for other reasons. Furthermore, the addition of nonionic surfactants would tend to reduce foam formation herein. Such materials tend to enhance performance of the other components of the composition, particularly useful nonionic surfactant for use as a defoamer is nonylphenol having an average of 12 moles of ethylene oxide condensed thereon, it being encapped with a hydrophobic portion comprising an average of 30 moles of propylene oxide.

Chelating agents can be added to the composition of the invention to enhance biological activity, cleaning performance and stability of the peroxyacids. For example, 1-hydroxyethylidene-1,1-diphosphonic acid commercially available from the Monsanto Company under the designation "DEQUEST" has been found to be effective. Chelating agents can be added to the present composition to control or sequester hardness ions such as calcium and magnesium. In this manner both detergency and sanitization capability can be enhanced.

Other materials which are sufficiently stable at the low pH contemplated by the present composition may be added to the composition to impart desirable qualities depending upon the intended ultimate use. For example, phosphoric acid ($H_3PO_4$) can be added to the composition of the invention. Additional compounds can be added to the concentrate (and thus ultimately to the use solution) to change its color or odor, to adjust its viscosity, to enhance its thermal (i.e., freeze-thaw) stability or to provide other qualities which tend to make it more marketable.

The composition of the invention can be made by combining by simply mixing an effective amount of a $C_8$–$C_{12}$ peroxyacid such as a peroxyfatty acid with some source of a $C_2$–$C_4$ peroxycarboxylic acid such as peroxyacetic acid. This composition would be formulated with preformed perfatty acid and preformed peroxyacetic acid. A preferred composition of the invention can be made by mixing a $C_2$–$C_4$ carboxylic acid, a $C_8$–$C_{12}$ carboxylic acid, a coupler and a stabilizer and reacting this mixture with hydrogen peroxide. A stable equilibrium mixture is produced containing a $C_2$–$C_4$ peroxycarboxylic acid and a $C_8$–$C_{12}$ peroxyacid by allowing the mixture to stand for from one to seven days at 15° C. to 25° C. As with any aqueous reaction of hydrogen peroxide with a free carboxylic acid, this gives a true equilibrium mixture. In this case, the equilibrium mixture will contain hydrogen peroxide, a $C_2$–$C_4$ peroxycarboxylic acid, a $C_8$–$C_{12}$ carboxylic acid, a $C_2$–$C_4$ peroxycarboxylic acid, a $C_8$–$C_{12}$ peroxyacid, water, and various couplers and stabilizers.

By using the above approach, the composition of the invention can be formulated by merely mixing readily available raw materials, e.g., acetic acid, hydrogen peroxide and fatty acid. By allowing solution time for equilibrium to be obtained, the product containing both of the active biocides is obtained. In varying the ratio of $C_2$–$C_4$ carboxylic acid to $C_8$–$C_{12}$ carboxylic acid, it is easy to vary the ratio of $C_2$–$C_4$ peroxycarboxylic acid to $C_8$–$C_{12}$ peroxyacid.

Method of Treatment

The present invention contemplates a concentrate composition which is diluted to a use solution prior to its utilization as a microbicide. Primarily for reasons of economics, the concentrate would normally be marketed and the end user would dilute the concentrate with water to a use solution. A preferred antimicrobial concentrate composition comprises about 0.1 to 20 wt. %, preferably about 0.1 to 5 wt. %, of a $C_8$–$C_{12}$ peroxyfatty acid, about 1 to 20 wt. % of a $C_2$–$C_4$ peroxycarboxylic acid, about 1 to 15 wt. % of a hydrotrope coupling agent, and about 1 to 30 wt. % of hydrogen peroxide. Other acidulants may optionally be employed in the composition such as phosphoric acid.

The level of active components in the concentrate composition is dependent upon the intended dilution factor and desired acidity in the use solution. The $C_8$–$C_{12}$ peroxyacid component is generally obtained by reacting a $C_8$–$C_{12}$ carboxylic acid with hydrogen peroxide in the presence of a $C_2$–$C_4$ carboxylic acid. The resulting concentrate is diluted with water to provide the use solution. Generally, a dilution of 1 fluid oz. to 4 gallons (i.e. dilution of 1 to 500 by volume) of water can be obtained with 2% to 20% total peracids in the concentrate.

The compositions of the invention can be applied to growing plant tissue in a variety of techniques. The aqueous solution can be sprayed, painted, daubed, fogged, flooded onto or into the plant, the plant hydroponic substrate, the agricultural earth. The material can be reapplied periodically as needed.

EXAMPLES

Initial testing

The examples given herein describe the treatment of a snow mold fungus isolated from a mountain ash (*Sorbus Americana*) tree. Testing consisted of an untreated control versus treating the fungus with peroxy acetic acid (POAA) ($C_2$) and peroxyacetic/peroxyoctanoic (POAA/POOA) ($C_2$/$C_8$) composition. This testing showed that the latter was very effective in killing the fungus.

Thus, approximately 10 $cm^2$ of “snow mold” was removed from the branch section and split it into three parts; putting each into water. One section was untreated. A second was treated with 500 ppm peroxyacetic acid, and a third was treated using a mixed peracid system ($C_2$/$C_8$). After two days:

1. The control was still thriving and very moist to the touch; with a large jelly-like volume of fungi.

2. The POAA sample treated was approximately ½ dead with what appears to be a dead outer crust over approximately ⅔ the sample and a dried completely dead patch over the rest. The ⅔ crusted area still had the soft jelly-like mass.

3. The C2/C8 penoxyacid blend treated Fungi appeared all dead and dried up. No mass of jelly left.

Peroxy Acetic Acids Effect On Growing Plant Tissue

The study was conducted on growing plant tissues using sprays done before 8:00 AM. Testing was conducted on usually disease free plants to investigate possible side effects such as burning of plant tissue. The data demonstrates both peracid compositions to be similar in effect to the growing plant tissue during application; with both being relatively inert on the tissue surfaces except for high surface area crops such as Asparagus leaves (no effect on stems).

| Peracid Formula | Dosed Peracid (ppm)[3] | Plant type/treated area | Observed effects 8 hrs after application |
|---|---|---|---|
| POAA[1] | 100 | American Basswood/ lower leaves | No changes, no burning or tissue damage |
| POAA/ POOA[2] | 100 | American Basswood/ lower leaves | No changes, no burning or tissue damage |
| POAA[1] | 100 | American Basswood/ lower leaves (approx. 30') | No changes, no burning or tissue damage |
| POAA/ POOA[2] | 100 | American Basswood/ lower leaves (approx. 30') | No changes, no burning or tissue damage |
| POAA[1] | 100 | State Fair Apple/whole tree (approx. 7') | No changes, no burning or tissue damage |
| POAA/ POOA[2] | 100 | State Fair Apple/whole tree (approx. 7') | No changes, no burning or tissue damage |
| POAA[1] | 100 | Wild rose bush/whole (3') | No changes, no burning or tissue damage |
| POAA/ POOA[2] | 100 | Wild rose bush/whole (2') | |
| POAA[1] | 100 | Asparagus/½ plant (approx. 4') | Some yellowing found, apparent leaf burn on treated halves |
| POAA/ POOA[2] | 100 | Asparagus/½ plant (approx. 4') | Some yellowing found, apparent leaf burn on treated halves |
| POAA[1] | 100 | Pixwell Gooseberry/ ½ plant (approx. 3') | No change |
| POAA/ POOA[2] | 100 | Pixwell Gooseberry/ ½ plant (approx. 3') | No change |

[1]POAA = peroxyacetic acid ($C_2$).
[2]POAA/POOA = peroxyacetic/peroxyoctanoic acids ($C_2$/$C_8$).
[3]Total active peracid.

Continued Tests For Peracids On Plant Tissue

| Peracid[A] | Dosed ppm | Plant/Area[B] | Comments |
|---|---|---|---|
| 1 | 100 | Basswood/lower branches | No effects noted, no burn or bleaching |
| 2 | 100 | Basswood/lower branches | No effects note, no burn or bleaching |
| 1 | 100 | Rose/whole | No effects noted, no burn or bleaching |
| 2 | 100 | Rose/whole | No effects noted, no burn or bleaching |
| 1 | 100 | ½ asparagus plant | Leaf yellowing and more bleaching - stopping application to avoid plant death |
| 2 | 100 | ½ asparagus plant | Leaf yellowing and more bleaching-stopping application to avoid plant |
| 1 | 100 | Beacon Apple/whole State Fair Apple/whole | No effect, as above |
| 2 | 100 | State Fair Apple/whole NOTE: switched application order vs. last week | No effect, as above |
| 1 | 100 | Gooseberry/half | No effect, as above |
| 2 | 100 | Gooseberry/half | No effect, as above |
| 1 | 100 | Pontiac Potato Plant/ whole | No effect, as above |
| 2 | 100 | Pontiac Potato Plant/ whole | No effect, as above |
| 1 | 100 | Beta Grapevine/ ½ vine | No effect, as above |
| 2 | 100 | Beta Grapevine/ ½ vine | No effect, as above |
| Increased Dosage Tests: | | | |
| | 300 | Wild Plum/approx. ½ tree | No effect, as above |
| 2 | 300 | Wild Plum/approx. ½ tree | No effect, as above |
| 1 | 300 | Pontiac Potato/whole | No effect, as above |
| 2 | 300 | Pontiac Potato/whole | No effect, as above |

[A]As per previous table
[B]Same test plants and test area as per previous table, unless noted.

| Peracid | Dosed ppm | Plant/Area | Comments |
|---|---|---|---|
| 1 | 300 | Approx. 10' Wild Plum/whole | No effect noticed, no burning or bleaching |
| 2 | 300 | Approx. 8' Wild Plum/whole | No effect noticed, no burning or bleaching |
| 1 | 300 | Red Pontiac/whole | Same as above - no effect |
| 2 | 300 | Red Pontiac/whole | Same as above no effect |
| 1 | 300 | Gooseberry/½ | Same as above - no effect |
| 2 | 300 | Gooseberry/½ | Same as above no effect |
| 1 | 300 | Beebalm (menarda)/10 plants | Slight leaf yellowing-killed snow mold on all plants-(approx. 16 with mold before treatment) |
| 2 | 300 | Beebalm (menarda)/10 plants | Slight leaf yellowing-killed snow mold on all plants-(approx. 16 with mold before treatment) |
| | 300 | Rose/whole | No effects, as above |
| 2 | 300 | Rose/whole | No effects, as above |
| 1 | 300 | Beacon Apple/whole | No effects, as above |
| 2 | 300 | State Fair Apple, whole | No effects, as above |
| 1 | 300 | American Basswood/ bottom | No effects, as above |
| 2 | 300 | American Basswood/ bottom | No effects, as above |
| 1 | 300 | Hawthorne (approx. 7[1])/whole | No effects, as above |
| 2 | 300 | Hawthorne (approx. 8 ½[1])/whole | No effects, as above |
| 1 | 300 | Betterboy Tomato/ whole | No effects, as above |
| 2 | 300 | Betterboy Tomato/whole | No effects, as above |
| 1 | 300 | Beta Grape/½ (10') vine | No effects, as above |
| | 300 | Beta Grape/½ (10') vine | No effects, as above |

minimum inhibitory concentrations against the *Botrytis cinera* ATCC 11542 plant pathogen organism.

*Botrytis cinera* culture was prepared by inoculating the center of ten Sabouraud Dextrose Agar filled dishes and incubating at 26° C–30° for 15 days. Mycelial mats were removed by adding 10 mL of sterile water and using a sterile spatula to brush the microbial growth from agar surface. The suspension was transferred to tissue grinder and macerated with 10–25 mL of sterile water, then filtered through cheesecloth and stored in a glass bottle at 4° C. until test time.

Product dilutions were prepared in a Sabouraud Dextrose broth at levels of % POAA adjusted to deliver a part per million consternation of 30, 45, 60, 75, 150 and 300. Solutions were inoculated with 0.5 mL of the prepared culture suspensions and incubated at 26° C–30° C. for 15 days to observe growth. One tube of Sabouraud Dextrose broth was used as a positive growth control for each culture, and 1 tube was used to observe sterility of broth.

Table 1 compares the minimum inhibitory concentration (the lowest peracid efficacy level to impart no growth in the plant pathogen) of the mixed peracid compositions (line 1) and those of the single peracid (lines 2) for the reduction of common plant pathogens. The results demonstrate the 5-fold improved efficacy results of the mixed peracid compositions for the reduction of *Botrytis cinera* ATCC 11542 (cf., lines 1 and 2); i.e., the minimum inhibitory concentration for controlling *Botrytis cinera* is 60 ppm peracid with the current formulas, while 300 ppm peracid is required using the prior art.

TABLE 1

Minimum Inhibitory Concentration of Peracetic Acid vs. a Novel Mixed Peracid Composition against *Botrytis cinera* Plant Pathogen

| | | | Minimum Inhibitory Concentration | | | | | |
|---|---|---|---|---|---|---|---|---|
| Run # | Peracid Test | Organism | 30 (ppm) | 45 (ppm) | 60 (ppm) | 75 (ppm) | 150 (ppm) | 300 (ppm) |
| current art: | | | | | | | | |
| 1 | Mixed Peracid Formula (POAA/ POOA)[1] | *Botrytis cinera* | + | + | – | – | – | – |
| prior art: | | | | | | | | |
| 2 | Prior Art (POAA)[3] | *Botrytis cinera* | + | + | + | + | + | – |

(–) = no growth, (+) = growth
[1]POAA/POOA = peroxyacetic/peroxyoctanoic acids
[2]prior art as demonstrated in GB 2187958A.
[3]POAA = peroxyaceticacid

WORKING EXAMPLES

Working Example 1

Minimum Inhibitory Concentration of Peracetic Acid vs. Mixed Peracid Composition against *Botrytis cinera* Plant Pathogen This example compares the effect of the prior art using peracetic acid (POAA) vs. the combination peracid formula of the present invention. The objective is to determine the

Working Example 2

Table 2 compares the antimicrobial effect of using the present mixed peracid system and prior known materials as fruit and vegetable treatments for human pathogen reduction. Thus, we compare the novel mixed $C_2/C_8$ peracid system to of using sodium hypochlorite or peracetic acid.

Testing was performed on three produce surfaces: tomatoes, leaf lettuce and apples, and also using four test organisms—*Listeria monocytogenes, Salmonella javiana,* natural bacteria flora, and *penicillium expansum*. For the pathogenic organisms, a 1:10 dilution of a $10^7$ CFU/mL test system suspension was prepared. 50 grams of the leaf lettuce, a whole tomato, or whole apple were placed into a plastic bag. Each bag was inoculated with 10.0 Ml test system suspension resulting in an inoculum level of $10^7$ CFU/mL (colony forming units per milliliter). Bags were gently shaken for even distribution of the test system for 5 minutes. The produce types were then stored overnight at 4° C. Untreated controls (no bacterial inoculum-10 mL of phosphate buffered dilution water) were also prepared. Two liter volumes of the test solutions were prepared in 4 liter beakers. Solutions were prepared in laboratory tap water to simulate industry conditions. The vegetables were then exposed to the test solution by submersion for 5 minutes at 72° F. At the end of the specified exposure time, the vegetables were removed from the test solution and thoroughly rinsed under fresh running tap water. Fifty grams of the vegetable (lettuce) or whole produce (tomato or apple)+ 100 mL buffered dilution water were placed into a stomacher bag. The vegetables were stomached (lettuce) or massaged (tomato or apple) for 60 seconds. Serial dilutions were made and plated on TGE (Salmonella), SAB (penicillium) and BHI (Listeria). Plates were incubated at 35° C. for 48 hours. The following controls were performed in each test: Untreated control (no inoculation, no chemical treatment) for the background microbial load, an inoculated control (inoculated but no chemical treatment) for the inoculum plus background microbial load on vegetable surface, and a tap Water control with a serial dilution to determine if microbial contamination was present in the rinse water or product dilutent.

The results demonstrate the enhanced effectiveness of the mixed peracid system vs. the conventional (sodium hypochlorite or peracetic acid) treatment systems. Thus, substantial improvements over the sodium hypochlorite treatments are found when using the peracid formulas. Additionally, the mixed peracid composition of the present invention ($C_2/C_8$) yields log reduction improvements of 0.5–1.0 log vs. a single $C_2$ peracid composition; or comparable log reductions using 50% less of the active peracids.

TABLE 2

The Comparative Effect Of A Mixed Peracid System vs. Prior Art For Effecting Microbial Control On Harvested Fruit And Vegetables

| Test # | Treated Produce & Test Organism | Treatment Process | Active Treatment Concentration (ppm) | Average Microbial Count (CFU/mL) | Log Reduction |
|---|---|---|---|---|---|
| | Tomatoes | | | | |
| 1 | *L. monocytogenes* | moculated control | 0 (control) | $4.8 \times 10^5$ | 0[1] |
| 2 | *L. monocytogenes* | peracetic acid[1] | 50 ppm POAA[1] | $1.4 \times 10^5$ | 0.5 |
| 3 | *L. monocytogenes* | novel mixed peracids[2] | 50 ppm (POAA + POOA)[2] | $2.4 \times 10^4$ | 1.3 |
| 4 | *S. javiana* | inoculated control | 0 (control) | $1.6 \times 10^6$ | 0 |
| 5 | *S. javiana* | sodium hypochlorite[3] | 25 ppm NaOCl[3] | $7.4 \times 10^6$ | 0.3 |
| 6 | *S. javiana* | peracetic acid[1] | 25 ppm POAA[1] | $1.7 \times 10^4$ | 2.0 |
| 7 | *S. javiana* | peracetic acid[1] | 50 ppm POAA[1] | $8.1 \times 10^3$ | 2.3 |
| 8 | *S. javiana* | peracetic acid[1] | 75 ppm POAA[1] | $4.6 \times 10^3$ | 2.5 |
| 9 | *S. javiana* | noval mixed peracids[2] | 50 ppm (POAA + POOA)[2] | $2.3 \times 10^3$ | 2.8 |
| | Lettuce | | | | |
| 10 | natural flora | untreated control[1] | 0 (control) | $1.3 \times 10^8$ | 0[1] |
| 11 | natural flora | sodium hypochlorite[3] | 100 ppm NaOCl[3] | $1.4 \times 10^8$ | 0.2 |
| 12 | natural flora | peracetic acid[1] | 75 ppm POAA[1] | $2.1 \times 10^7$ | 1.0 |
| 13 | natural flora | novel mixed peracids[2] | 50 ppm (POAA + POOA)[2] | $1.8 \times 10^7$ | 1.1 |
| | Apple | | | | |
| 14 | *P. expansum* | inoculated control | 0 (control) | $2.8 \times 10^4$ | 0[1] |
| 15 | *P. expansum* | peracetic acid[1] | 80 ppm POAA[1] | $7.5 \times 10^3$ | 0.6 |
| 16 | *P. expansum* | novel mixed peracids[2] | 80 ppm (POAA + POOA)[2] | 1.4 x i03 | 1.3 |

[1]per prior art GB 2187958A
[1]No treatment control
[2]present invention
[3]chlorine washes

Working Example 3

Temperature Effects For Mixed Peracid Compositions

Example 3 compares the temperature effect of using peracetic acid (POAA) vs. a mixed peracid system under cold water applications. The experiments were run as in example 2; however, a cold water (40° F.) application temperature was used.

In contrast to the experiments of Table 2 where peracetic acid applications outperformed sodium hypochlorite for surface reduction of microbials, the results of Table 3 demonstrate that colder treatment temperatures impedes the activity of the single peracid composition. Conversely, the mixed peracid system is unexpectedly less effected, and still substantially outperforms the known systems.

TABLE 3

| Temperature Evaluation For Peracid Treatment of Tomatoes | | | |
|---|---|---|---|
| Run # | Treatment Condition (all at 40° F.) | Peracid Treatment Level (ppm) | Log Reduction (of *S. javiana*) on Tomatoes |
| prior art examples: | | | |
| 1 | Sodium Hypochlorite | 80 ppm | 1.4 |
| 2 | Peracetic Acid | 80 ppm | 0.0 |
| current art example: | | | |
| 3 | Peracetic-Peroctanoic Acid Mix | 80 ppm | 2.3 |

Working Example 4

Comparative Peracid Treatment of a Substrate vs. Alfalfa Sprouts For Microbial Control During Hydroponic Growing The objective of this example was to compare the use of a single peracid vs. mixed peracids for microbial reduction during hydroponic growth of alfalfa sprouts. Ongoing concern in the industry is the control of microbial populations; especially human and plant patogenics, but also nutrition-solution molds and fungi. The following test as conducted to determine potential microbial control during the hydroponic growing cycle.

Table 4 compares the results of utilizing the continuous hydroponic treatment technique of the present invention in contrast to U.S. Pat. No. 5,168,655 which utilizes peracetic acid disinfection of hydroponic substrates; i.e., substantial (>5-log) microbial reductions can be found if the peracid treatment is ongoing vs. essentially no reduction if only the substrate is treated to hydroponic growth.

TABLE 4

Peracetic Acid (POAA) and Peracetic-Peroctanoic (POAA-POOA) Treatments of Alfalfa Sprouts comparing The Prior and Current Art Aerobic Plate Count Results

| | 1 | 2 | 3 | 4 | 5 | 6 |
|---|---|---|---|---|---|---|
| | | | Microbial Reduction[1] | | | |
| | Peracid Treatment Condition | Peracid Concentration (ppm) | Day 1 | Day 2 | Day 3 | Day 4 |
| | Control Study | | | | | |
| 1 | Water Control (no peracid treatment)[2] | 0 | 0 | 0 | 0 | 0 |
| | Current Art Examples | | | | | |
| 6 | POAA-POOA treated[3] | 40 ppm | 1.5 | <0.1 | no reduction | no reduction |
| 7 | | 80 ppm | 1.8 | 1.9 | 0.5 | 0.2 |
| 8 | | 160 ppm | 1.9 | 5.4 | 3.1 | 2.9 |
| 9 | | 320 ppm | 1.6 | 5.9 | 5.0 | 2.5 |
| | Prior Art Examples | | | | | |
| 9 | POAA treated substrate[4] | 40 ppm | <0.5 | no | no | no |
| 10 | | 80 ppm | <0.5 | reduction | reduction | reduction |
| 11 | | 160 ppm | <0.5 | at any | at any | at any |
| | | 320 ppm | <0.5 | level | level | level |

[1]Microbial reduction vs. the water control study without any type of peracid treatment

[2]The water control was used as the background basis for the treatment efficiency Log reductions for each treatment day. Typically log counts of ~1 × $10^9$ cfu/ml were found.

[3]POAA-POOA = peroxyacetic acid from an equilibrium composition, using the method of application of US 5,168,655.

[4]POAA = peroxyacetic-peroxyoctanoic acids from an equilibrium composition, using the current art method of application.

Working Example 5

POAA and POAA-POOA Treatment of Alfalfa Sprouts with Variable Concentrations of Peracids The objective of this example was to evaluate microbial reduction using peracid misting during the daily hydroponic growth of alfalfa sprouts; against natural bacterial flora. Commercially, bean and alfalfa sprouts are grown by overhead misting of seed plates for 3–5 days. The sprouts are harvested and the seed waste disposed of. An ongoing concern in the industry is the control of microbial populations; especially human and plant pathogenics, but also nutrition-solution molds and fungi. The following test was conducted to determine potential microbial control during the hydroponic growing cycle.

The alfalfa sprouts were soaked in various concentrations of equilibrium obtained peracetic (POAA) or peracetic-peroctanoic POAA-POOA solutions. One sample was soaked in water as a control. The following morning the alfalfa sprouts were placed into a sterile petri dish by evenly spreading the seeds on the bottom of the dish. The petri dishes were covered with cheese cloth for the growing procedure.

During growing (days 1–4) the alfalfa seeds were treated twice daily at 8:00 AM and 4:45 PM by misting with 10 ml of the same concentration of peracid in which they were soaked. The water control was misted with water. Microbial samplings were taken at 8:00 AM each of the 4 treatment days. A 1:10, wt:wt, mixture of sprout:water was stomached and plated onto TGE Agar subculture media using a Pour Plate Technique with phosphate buffered dilutions of $10^{-3}$, $10^{-5}$, $10^{-7}$. After 48 hours at 35° C. the micro results were determined and are shown in Table 2:

The results of Table 5 demonstrate the ability to effect microbial populations during hydroponic growth of plant tissue using continuous peracid applications. In contrast to U.S. Pat. No. 5,168,655 which utilizes peracetic acid disinfection of hydroponic substrates prior to a crop production cycle, the microbial peracids of the present invention demonstrates the novel utility of using peracids to effect continuous microbial control during the entire hydroponic growth cycle, without loss to crop yield (see examples 4 and 5). The data also indicates the need to modify the dosing procedure to enhance the microbial reduction near the end of the hydroponic cycle. This hypothesis is tested in Example 3.

procedure during the daily hydroponic growth of alfalfa sprouts; against natural bacterial flora. This should allow for a lower dosage profile of peracids.

Using the above microbial technique, the alfalfa sprouts were soaked in 80 ppm of POAA or POAA-POOA solutions. One sample was soaked in water as a control. The following morning the alfalfa sprouts were placed into a sterile petri dish by evenly spreading the seeds on the bottom of the dish. The petri dishes were covered with cheese cloth for the growing procedure.

During growing (days 1–4) the alfalfa seeds were treated from 8:00 Am to 3:00 PM on an hourly basis by misting with 10 ml of the same concentration of peracid in which they were soaked. The water control was misted with water. Microbial samplings were taken at 4:00 PM each of the 4 treatment days.

The results of Table 6 demonstrate the improved efficacy of: using a more continuous dosing system, and for using a mixed peracid system for microbial control during hydroponic growth of plant tissue. While peracetic acid can impart an initial (day 1–2) microbial reduction vs. the control (cf., experiment 1,2), it fails after the 2nd growing day. Conversely the mixed peracetic-peroctanoic acid (POAA-POOA) system yields continuous microbial control (>20log) over the entire sprout growing time (experiment 3). For all the experiments the germination rate of the seed was greater than 95%.

TABLE 5

Peracetic Acid (POAA) and Peracetic-Peroctanoic (POAA-POOA) Treatments of Alfalfa Sprouts Using Variable Treatment Concentrations
Aerobic Plate Count Results

| | 1<br>Peracid Treatment Condition | 2<br>Peracid Concentration (ppm) | 3<br>Microbial Reduction[1]<br>Day 1 | 4<br><br>Day 2 | 5<br><br>Day 3 | 6<br><br>Day 4 |
|---|---|---|---|---|---|---|
| 1 | Water Control (no peracid treatment)[a] | 0 | 0 | 0 | 0 | 0 |
| 2 | POAA treated[b] | 40 ppm | 0.4 | 0.1 | no reduction | no reduction |
| 3 | | 80 ppm | 1.7 | 0.5 | 0.2 | 0.1 |
| 4 | | 160 ppm | 1.9 | 2.2 | 0.4 | 0.2 |
| 5 | | 320 ppm | 1.7 | 4.7 | 4.2 | 0.3 |
| 6 | POAA-POOA treated[c] | 40 ppm | 1.5 | <0.1 | no reduction | no reduction |
| 7 | | 80 ppm | 1.8 | 1.9 | 0.5 | 0.2 |
| 8 | | 160 ppm | I.9 | 5.4 | 3.1 | 2.9 |
| 9 | | 320 ppm | 1.6 | 5.9 | 5.0 | 2.5 |

[a]The water control was used as the background basis for the treatment efficiency Log reductions for each treatment day. Typically $10^9$ cfu/ml.
[b]POAA = peroxyacetic acid from an equilibrium composition.
[c]POAA-POOA = peroxyacetic-peroxyoctanoic acids from an equilibrium composition.

Working Example 6

POAA and POAA-POOA Treatment of Alfalfa Sprouts with an Alternative Misting Procedure The objective of this example was to evaluate microbial reduction using a more continuous (hourly) peracid misting

TABLE 6

Peracetic Acid (POAA) and Peracetic-Peroctanoic (POAA-POOA) Treatments of Alfalfa Sprouts Using A Seven Hour Per Day Misting Procedure
Aerobic Plate Count Results

| | | 1<br>Day 1 | 2<br> | 3<br>Day 2 | 4<br> | 5<br>Day 3 | 6<br> | 7<br>Day 4 | 8<br> |
|---|---|---|---|---|---|---|---|---|---|
| | Sample Identification | CFU/ml | Log R[a] | CFU/ml | Log R[a] | CFU/ml | Log R[a] | CFU/ml | Log R[a] |
| 1 | Water Control | $2.0 \times 10^8$ | 0[b] | $1.1 \times 10^9$ | 0[b] | $7.8 \times 10^8$ | 0[b] | $2.1 \times 10^9$ | |

TABLE 6-continued

Peracetic Acid (POAA) and Peracetic-Peroctanoic (POAA-POOA) Treatments of Alfalfa Sprouts Using A Seven Hour Per Day Misting Procedure
Aerobic Plate Count Results

| | | 1 | 2 | 3 | 4 | 5 | 6 | 7 | 8 |
|---|---|---|---|---|---|---|---|---|---|
| | | Day 1 | | Day 2 | | Day 3 | | Day 4 | |
| | Sample Identification | CFU/ml | Log R[a] | CFU/ml | Log R[a] | CFU/ml | Log R[a] | CFU/ml | Log R[a] |
| 2 | peracetic acid (POAA) 80 ppm | $2.5 \times 10^6$ | 1.9 | $3.1 \times 10^8$ | 0.6 | $8.7 \times 10^8$ | no red[c] | $2.1 \times 10^9$ | no red |
| 3 | peracetic-peroctanoic acids (POAA-POOA) 80 ppm | $4.0 \times 10^4$ | 3.7 | $8.0 \times 10^6$ | 2.1 | $6.5 \times 10^6$ | 2.1 | $1.3 \times 10^7$ | 2.2 |

[a]Log R = log reduction.
[b]The water control was used as the background basis for the treatment efficiency Log reductions.
[c]no red = no reduction of the microbial load within the testing error range.

Working Example 7

POAA and POAA-POOA Continuous Misting Treatments of Alfalfa Sprouts

The objective of this example was to evaluate microbial reduction using a continuous (hourly over 24-hours) peracid misting procedure during the daily hydroponic growth of alfalfa sprouts; against natural bacterial flora.

Using the above microbial technique, the alfalfa sprouts were soaked in 80 ppm or POAA or POAA-POOA solutions. One sample was soaked in water as a control. The following morning the alfalfa sprouts were placed into a sterile petri dish by evenly spreading the seeds on the bottom of the dish. The petri dishes were covered with cheese cloth or the growing procedure.

During growing (days 104) the alfalfa seeds were treated on an hourly basis (over the entire 24 hour day) by misting with 10 ml of the same concentration of peracid in which they were soaked. The water control was misted with water. Microbial samplings were taken at 4:00 PM each of the 4 treatment days.

The results of Table 7 demonstrates the unexpected result that continuous 24 hour per day misting does not improve—over the previous examples 7-times per day peracid application—the final growing day microbial control efficacy for either peracid system during hydroponic production of plant tissue (cf., Table 6, experiments 2,3 vs. Table 7 experiment 2,3). Additionally, the germination yield dropped off tremendously (<50%) in all the 24-hour per day studies as compared to the results of example 3.

TABLE 7

Peracetic Acid (POAA) and Peracetic-Peroctanoic (POAA-POOA) Treatments of Alfalfa Sprouts Using a Twenty Four Hour Per Day Misting Procedure
Aerobic Plate Count Results

| | | 1 | 2 | 3 |
|---|---|---|---|---|
| | | Day 4 results | | |
| | Sample Identification | Microbial CFU/mL | Log R[a] | Germination rate[b] |
| 1 | Water Control | $1.0 \times 10^8$ | 0[C] | <50% |
| 2 | peracetic acid (POAA) 80 ppm | $6.0 \times 10^7$ | 0.2 | <50% |

TABLE 7-continued

Peracetic Acid (POAA) and Peracetic-Peroctanoic (POAA-POOA) Treatments of Alfalfa Sprouts Using a Twenty Four Hour Per Day Misting Procedure
Aerobic Plate Count Results

| | | 1 | 2 | 3 |
|---|---|---|---|---|
| | | Day 4 results | | |
| | Sample Identification | Microbial CFU/mL | Log R[a] | Germination rate[b] |
| 3 | peracetic-peroctanoic acids (POAA-POOA) 80 ppm | $3.5 \times 10^6$ | 1.9 | <40% |

[a)]Log R = log reduction.
[b)]A visual evaluation of % of seeds growing vs. non sprouted.
[c)]The water control was used as the background basis for the treatment efficiency Log reductions.

Working Example 8

POAA and POAA-POOA Daily Misting Germination Rates of Alfalfa Sprouts

The objective of this example was to evaluate the germination rate for the various peracid applications during the hydroponic growing cycle of alfalfa sprouts.

Using the above microbial technique, the alfalfa sprouts were soaked in 80 ppm of POAA or POAA-POOA solutions. One sample was soaked in water as a control. The following morning the alfalfa sprouts were placed into a sterile petri dish by evenly spreading the seeds on the bottom of the dish. The petri dishes were covered with cheese cloth for he growing procedure.

During growing (days 1–4) the alfalfa seeds were treated using various application times as per examples 2–4 by misting with 10 ml of the same concentration of peracid in which they were soaked. The water control was misted with water. After 4 days the germination rate was visually determined.

The results of Table 8 demonstrate: that proper selection of the application rate and peracid composition is necessary to impart both microbial reduction and hydroponic seed germination. Both upper and lower application limits are found.

TABLE 8

Peracetic Acid (POAA) and Peracetic-Peroctanoic (POAA-POOA) Treatments of Alfalfa Sprouts Using Variable Treatment rates Aerobic Plate Count Results

| | Peracid Treatment Rate | 1<br>2 treatments per day | 2<br>Day 4 Microbial and Germination Results<br>(Log Reduction and %)[a]<br>7 treatments per day | 3<br>24 treatments per day |
|---|---|---|---|---|
| 1 | POAA treated, Log Reduction[b] | 0 | 0 | 0.2 |
| 2 | POAA-POOA treated, Log Reduction[b] | <0.1 | 2.2 | 1.9 |
| 3 | POAA treated, % Germination[c] | >95% | >95% | <50% |
| 4 | POAA-POOA treated, % Germination[c] | >95% | >95% | <80% |

[a]The water control was used as the background basis for the treatment efficiency Log reduction at the end of the treatment cycle.
[b]Log reduction vs. the water control.
[c]% Germination as per visual evaluation of % non-sprouted seeds.

Working Example 9

Hydroponic POAA and POAA-POOA Treatments of Alfalfa Sprouts With a Pre-dosing Misting Procedure The objective of this example was to evaluate microbial reduction using a predosing of a peracid(s), followed by subsequent water-only mistings during the daily Hydroponic growth of alfalfa sprouts; against natural bacterial flora. Again, this allows for a lower overall dosage profile of peracids.

Using the above microbial technique, the alfalfa sprouts were soaked in 80 ppm of POAA or POAA-POOA solutions for 16 hours. One sample was soaked in water as a control. The following morning the alfalfa sprouts were placed into a sterile petri dish by evenly spreading the seeds on the bottom of the dish. The petri dishes were covered with cheese cloth for the growing procedure.

During growing (days 1–4) the alfalfa seeds were treated from 8:00 AM to 3:00 PM on an hourly basis by misting with water only (no peracids in these subsequent Hydroponic growth cycles). Likewise, the water control was misted with water. Microbial samplings were taken at 4:00 PM each of the 4 treatment days.

The results of Table 9 demonstrate that the peracid systems impart a residual antimicrobial effect over the entire Hydroponic growing cycle. Surprisingly, the mixed peracid system yields a much improved efficacy verses the peracetic-alone formula; i.e., while peracetic acid can impart an initial (day 1) microbial reduction (>1-log) vs. the control (cf., experiment 1,2), it fails after the 2nd growing day. Conversely the mixed peracetic-peroctanoic acid (POAA-POOA) system yields continuous microbial control (>2-log) over the entire sprout growing time (experiment 3) even though the growing seeds were only inoculated in the peracid formula. For all the experiments the germination rate of the seed was greater than 95%.

TABLE 9

Peracetic Acid (POAA) and Peracetic-Peroctanoic (POAA-POOA) Treatments of Alfalfa Sprouts Using A Single Misting Procedure Aerobic Plate Count Results

| | Sample Identification | 1<br>Day 1<br>CFU/ml | 2<br>Day 1<br>Log R[a] | 3<br>Day 2<br>CFU/ml | 4<br>Day 2<br>Log R[a] | 5<br>Day 3<br>CFU/ml | 6<br>Day 3<br>Log R[a] | 7<br>Day 4<br>CFU/ml | 8<br>Day 4<br>Log R[a] |
|---|---|---|---|---|---|---|---|---|---|
| 1 | Water Control | $2.0 \times 10^6$ | 0[b] | $7.0 \times 10^6$ | 0[b] | $5.8 \times 10^8$ | 0[b] | $5.2 \times 10^8$ | 0[b] |
| 2 | peracetic acid (POAA) 80 ppm | $9.4 \times 10^4$ | 1.3 | $1.8 \times 10^6$ | 0.6 | $2.9 \times 10^8$ | 0.3 | $3.9 \times 10^8$ | 0.1 |
| 3 | peracetic-peroctanoic acids (POAA-POOA) 80 ppm | $1.8 \times 10^4$ | 2.1 | $8.0 \times 10^3$ | 2.9 | $1.0 \times 10^6$ | 2.8 | $5.0 \times 10^5$ | 2.0 |

[a]Log R = log reduction.
[b]The water control was used as the background basis for the treatment efficiency Log reductions.

We claim:

1. A method of controlling microbial pathogens on living plant tissue comprising treating said plant tissue with a dilute aqueous solution comprising at least about 4 parts per million (ppm) of a $C_2$–$C_4$ peroxycarboxylic acid and at least about 1 part per million (ppm) of an aliphatic $C_8$–$C_{12}$ peroxycarboxylic acid.

2. The method of claim 1 wherein the plant tissue comprises a seed.

3. The method of claim 1 wherein the plant tissue comprises a tuber.

4. The method of claim 1 wherein the plant tissue comprises a growing plant.

5. The method of claim 1 wherein the plant tissue comprises a cutting.

6. The method of claim 1 wherein the plant tissue comprises rooting stock.

7. The method of claim 1, wherein said $C_2$–$C_4$ peroxycarboxylic acid is peroxyacetic acid.

8. The method of claim 1 wherein said $C_8$–$C_{12}$ aliphatic peroxycarboxylic acid is peroxyoctanoic acid.

9. A process for controlling fungi and microbial plant pathogens in growing plants comprising:

(a) diluting in an aqueous liquid a concentrate comprising:

(i) about 1 to 20 wt-% of a $C_2$–$C_4$ peroxycarboxylic acid; and (ii) about 0.1 to 20 wt-% of an aliphatic $C_8$–$C_{12}$ peroxycarboxylic acid to form a solution; and (b) contacting said growing plants with said solution.

10. The process of claim 9, wherein the $C_2$–$C_4$ peroxycarboxylic acid is peroxyacetic acid.

11. The process of claim 9, wherein the $C_8$–$C_{12}$ aliphatic peroxycarboxylic acid is peroxyoctanoic acid.

12. The process of claim 9, wherein the concentrate further comprises about 1 to 15 wt-% of a hydrotrope.

13. The process of claim 12, wherein the hydrotrope is n-octanesulfonate, a xylene sulfonate, a naphthalene sulfonate, an amine oxide or a mixture thereof.

14. The process of claim 9, wherein the concentrate further comprises a chelating agent.

15. The process of claim 14, wherein the chelating agent is 1-hydroxyethylidene-1,1-diphosphonic acid.

16. A process for controlling fungi and microbial plant pathogens in growing plants comprising:

(a) diluting in an aqueous liquid a concentrate comprising:

(i) about 1 to 20 wt-% of a $C_2$–$C_4$ peroxycarboxylic acid; and (ii) about 0.1 to 20 wt-% of an aliphatic $C_8$–$C_{12}$ peroxycarboxylic acid;

(iii) about 5 to 40 wt-% of a $C_2$–$C_4$ carboxylic acid;

(iv) about 1 to 20 wt-% of an aliphatic $C_8$–$C_{12}$ carboxylic acid; and (v) about 1 to 30 wt-% of hydrogen peroxide to form a solution; and (b) contacting said growing plants with said solution.

17. The process of claim 16, wherein the $C_2$–$C_4$ peroxycarboxylic acid is peroxyacetic acid.

18. The process of claim 16, wherein the $C_8$–$C_{12}$ aliphatic peroxycarboxylic acid is peroxyoctanoic acid.

19. The process of claim 16, wherein the concentrate further comprises about 1 to 15 wt-% of a hydrotrope.

20. The process of claim 16, wherein the hydrotrope is n-octanesulfonate, a xylene sulfonate, a naphthalene sulfonate, an amine oxide or a mixture thereof.

21. The process of claim 16, herein the concentrate further comprises a chelating agent.

22. The process of claim 21, wherein the chelating agent is 1-hydroxyethylidene-1,1-diphosphonic acid.

23. The process of claim 16, wherein said $C_2$–$C_4$ carboxylic is acetic acid.

24. The process of claim 16, wherein said aliphatic $C_8$–$C_{12}$ carboxylic acid is octanoic acid.

* * * * *

UNITED STATES PATENT AND TRADEMARK OFFICE
CERTIFICATE OF CORRECTION

PATENT NO. : 6,165,483
DATED : December 26, 2000
INVENTOR(S) : Hei et al.

It is certified that error appears in the above-identified patent and that said Letters Patent is hereby corrected as shown below:

Column 8,
Line 39, "a $C_2$–$C_4$ peroxycarboxylic" should read -- a $C_2$–$C_4$ carboxylic --

Column 12,
Line 16, "consternation" should read -- concentration --

Column 14,
Table 2, Test #1, "moculated control" should read -- inoculated control --
Table 2, Test #5, "7.4 x $10^6$" should read -- 7.4 x $10^5$ --
Table 2, Test #16, "1.4 x i03" should read -- 1.4 x $10^3$ --

Column 15,
Line 67, "patogenic" should read -- pathogens --

Column 16,
Line 1, "test as" should read -- test was --

Column 19,
Line 31, "80 ppm or" should read -- 80 ppm of --
Line 36, "cloth or" should read -- cloth for --
Line 38, "days 104" should read -- days 1-4 --

Column 20,
Line 54, "for he" should read -- for the --

Column 22,
Line 56, "$C_8$–$C_2$" should read -- $C_8$–$C_{12}$ --

UNITED STATES PATENT AND TRADEMARK OFFICE

CERTIFICATE OF CORRECTION

PATENT NO. : 6,165,483
DATED : December 26, 2000
INVENTOR(S) : Hei et al.

It is certified that error appears in the above-identified patent and that said Letters Patent is hereby corrected as shown below:

<u>Column 24,</u>
Line 20, "herein" should read -- wherein --

Signed and Sealed this

Eleventh Day of June, 2002

*Attest:*

JAMES E. ROGAN

*Attesting Officer* *Director of the United States Patent and Trademark Office*